Figure 1:
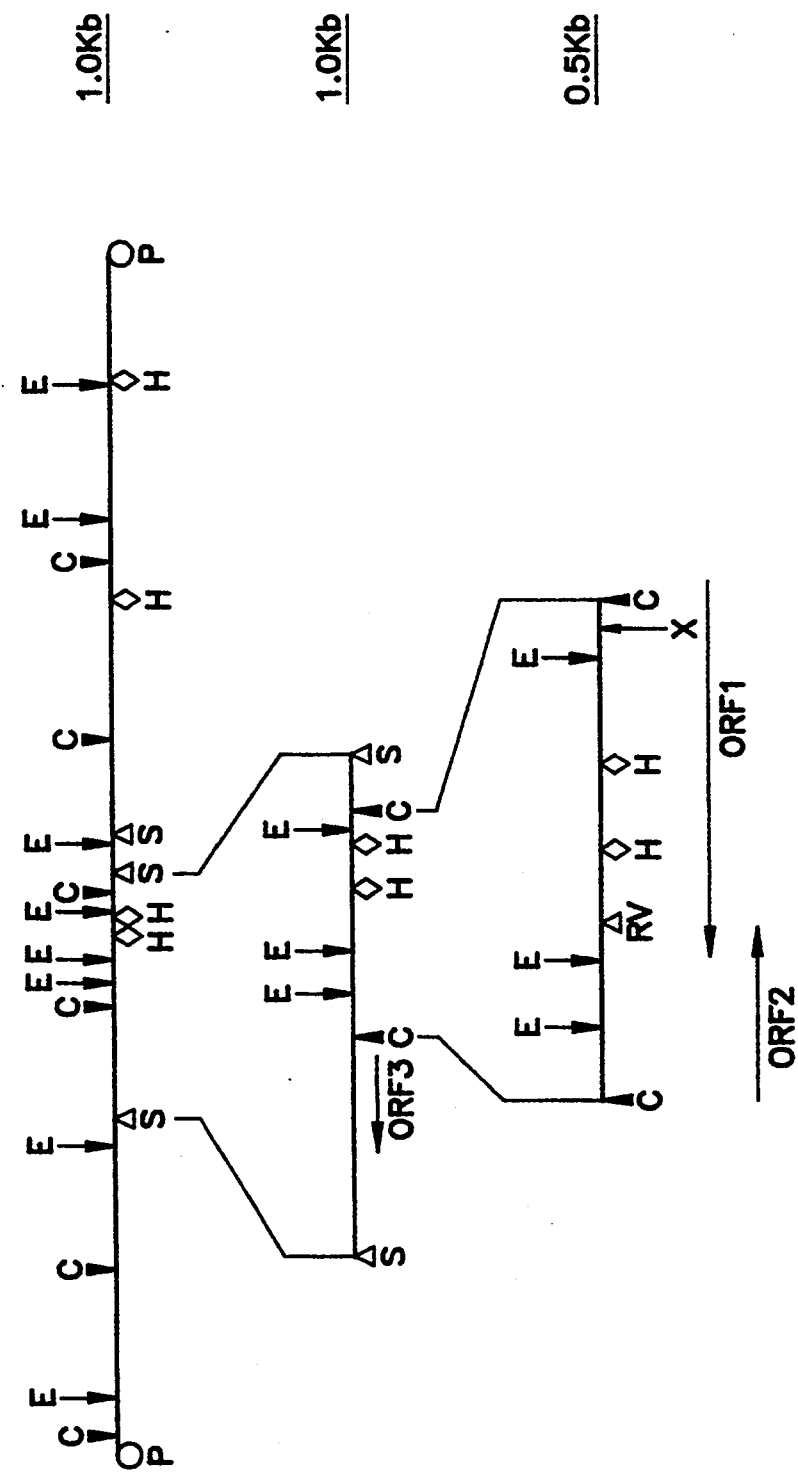

United States Patent [19]
Boyle et al.

[11] Patent Number: 5,368,855
[45] Date of Patent: * Nov. 29, 1994

[54] POX VIRUS VACCINE

[75] Inventors: David B. Boyle, Leopold; Sharad Kumar, Herne Hill, both of Australia

[73] Assignee: Commonwealth Science and Industrial Research Organisation, Campbell, Australia

[*] Notice: The portion of the term of this patent subsequent to Nov. 2, 2010 has been disclaimed.

[21] Appl. No.: 993,073

[22] Filed: Dec. 18, 1992

Related U.S. Application Data

[63] Continuation of Ser. No. 582,881, Oct. 9, 1990, Pat. No. 5,258,294.

[30] Foreign Application Priority Data

Feb. 12, 1988 [AU] Australia .................. PI6721

[51] Int. Cl.$^5$ .................. A61K 39/275; A61K 39/295
[52] U.S. Cl. .................. 435/320.1; 424/93.2; 424/199.1; 424/816; 935/65
[58] Field of Search ............... 424/89, 93 A; 536/24.1; 435/320.1, 172.3, 235.1; 935/6, 8, 32, 65, 36

[56] References Cited

U.S. PATENT DOCUMENTS 5,174,993 12/1992 Paoletti .................. 424/89

OTHER PUBLICATIONS

Boyle et al., "Identification and Cloning of the Fowlpox Virus Thymidine Kinase Gene Using Vaccinia Virus", *J. Gen. Virol.*, 67:1591–1600 (1986).
Boyle et al., "Fowlpox Virus Thymidine Kinase: Nucleotide Sequence and Relationships to Other Thymidine Kinases", *Virology*, 156:355–365 (1987).
Boyle et al., "Construction of Recombinant Fowlpox Viruses as Vectors for Poultry Vaccines", *Virus Research*, 10:343–356 (1988).
Hudson et al., "Genomic Structure of the Large RNA Segment of Infectious Bursal Disease Virus", *Nucleic Acids Res.*, 14:5001–5012 (1986).
Firth, "Occurrence of an Infectious Bursal Syndrome within an Australian Poultry Flock", *Aust. Vet. J.*, 50:128 (1974).
Fahey et al., "Characterization of Western Blotting of the Immunogens of Infectious Bursal Disease Virus", *J. Gen. Virol.*, 66:1479–1488 (1985).
Fahey et al., "Assessment of ELISA of Passively Acquired Protection Against Infectious Bursal Disease Virus in Chickens", *Aus. Vet. J.*, 64:203 (1987).
Azad et al., "Deletion Mapping and Expression of *Escherichia coli* of the Large Genomic Segment of a Birnavirus", *Virology*, 161:145–152 (1987).
Millar et al., "Nucleotide Sequence Analysis of the Haemagglutinin–Neuraminidase Gene of Newcastle Disease Virus", *J. Gen. Virol.*, 67:1917–1927 (1986).
Albiston and Gorrie, "Newcastle Disease in Victoria", *Aus. Vet. J.*, 18:75–79 (1942).
Morgan, A. J. et al. 1988 J. Med. Virol. vol. 25 pp. 189–195.
Conpar, Beh et al. 1986, Eur. J. Immunol. vol. 16 pp. 1479–1487.
Wachsman, M. et al. 1989, J. Infect. Diseases vol. 159 pp. 625–634.
Tsao, H. et al. 1988 J. Virol. vol. 62 pp. 4832–4834.
Boyle, D. B. et al. 1987, Virology vol. 156 pp. 355–365.
Venkatesan, S. et al. 1981 Cell vol. 125 pp. 801–813.
Wittek, R. et al. 1984 J. Virol. vol. 49 pp. 371–378.
Bertholet, C. et al. 1985 Proc. Natl. Acad. Sci. USA vol. 82 pp. 2096–2100.
Chakrabarti, S. et al. 1985 Molec. Cell. Biol. vol. 5 pp. 3403–3409.

*Primary Examiner*—Christine M. Nucker
*Assistant Examiner*—Mary E. Mosher
*Attorney, Agent, or Firm*—Merchant, Gould, Smith, Edell, Welter & Schmidt

[57] ABSTRACT

A gene sequence including a first promoter for the expression of a major early fowlpox virus (FPV) protein. In a preferred aspect, the gene sequence further includes a second promoter for the expression of a late fowlpox virus protein in opposite orientation to said first promoter. The promoter is useful in developing FPV based vectors for the delivery of vaccine antigens preferably to poultry, and as a tool to study the temporal regulation of poxvirus genes. The invention also offers methods useful in the construction of recombinant fowlpox viruses or related avian poxviruses, which methods are characterized by the introduction of foreign DNA into the fowlpox virus or into virus DNA sequences, which sequences are able to use native FPV promoter regions.

4 Claims, 13 Drawing Sheets

FIG. 3

```
          10         20         30         40         50         60
GGTCCTAAAT TTTGGTGGAT AAGGCAAATT ACTGCTTGT TGATTGTTAA ATCTATTAAG 70         80         90        100        110        120
AAAACTGGTA AAAATACCAG CAGTATCGTT ACTACGTAAT ATAGATATCA TTCTATCCTG 130        140        150        160        170        180
AATAGACCTA CTATCGTCTG TATTGTATTC GTCTACTATA GATTCCTTCT CATTTCTACT
                                          AccI            PRIMER 4

190        200        210        220        230        240
ATCATCTTCA CTGAAAATAT CTCTGGATTA CTCTGGATTA TTACTAAACAT TACGTTTGAT 250        260        270        280        290        300
TCTAGAAATA AAATCTTTGT GGAAGTTCTC AGCCATTTAG TATCCTAAAA TTGAATTGTA
                                          ORF 3

310        320        330        340        350        360
ATTATCGATA ATAAATGGAC AATTCTATGG ATATTAAACGA TATACTACTG TCAGATGATA
    ClaI       ORF 2

370        380        390        400        410        420
ACGATTATAA GAGTTACGAT GAAGATGATG ACTCTATATC CGATATAGGA GAAACAAGTG
                                                      PRIMER 3

430        440        450        460        470        480
ATGATTGTTG TACGACTAAA CAATCGGATT CCAGGATAGA ATCTTTCAAG TTTCGATGAAA 490        500        510        520        530        540
CTACTCAATC ACCTCATCCA AAACAATTGA GCGAAAGGAT AAAGGCTATA AAACAACGAT 550        560        570        580        590        600
ACACTAGACG TATAAGCCTA TTTGAAATAA CTGGAATTTT ATCCGAAAGT TATAATTTAT
```

FIG. 3A

```
       610        620        630        640        650        660
TACAACGTGG AAGAATTCCA TTACTTAATG ACCTGACAGA AGAAACGTTT AAAGATTCAA
            EcoRI
       670        680        690        700        710        720
TTATTAATAT TATGTTTAAA GAAATAGAAC AAGGAAATTG TCCTATAGTT ATACAAAAGA 730        740        750        760        770        780
ATGGAGAACT TTTATCCTTA ACCGACTTTG ATAAAAAAGG AGTACAGTAT CATCGGACTT 790        800        810        820        830        840
ACATTAAAAC AACCAACGTA TATATGGCGT AATTATAATT TAGATATATA ATGTCTTGAT
                                        ORF1→ ←ORF2
       850        860        870        880        890        900
ATAAAATCGA ATATGAATTC TATATCTACA GCATTTTCTT TATAGTTAAT GTTGTAATTA
            EcoRI
       910        920        930        940        950        960
TCGGTTATAC ATTGAACAAT TGATATAAGT GTTGTTTTGT GCTTTTCATA TTCTTCCACA 970        980        990       1000       1010       1020
AATATGTTTT TATACATTTC ACGGTTATTT GATATCTCAC TTATCAATCC CTGAATGTTA 1030       1040       1050       1060       1070       1080
TTAACCTTTC TTTTCTTTAA ATCTTCTACG GAAACTTTAG TCTTAAATGA TGCCATTATT 1090       1100       1110       1120       1130       1140
TCACTAAAAA GAACGTGTAA GCGTTCGTTA GTAAGTATTT CAGAATACAC TATACTAGAG
```

FIG. 3B

```
1150       1160       1170       1180       1190       1200
AGTTTAGAAA ATATGTTAAC AAATTGTGTT GTTTTGACAC AGCTAGTTTG AAATAAAATA 1210       1220       1230       1240       1250       1260
ATATTAGGTA ATACCTTTTT AAAGAAGCTT ACGTATTTAT TATTTATCTG GTCTATACCG 1270       1280       1290       1300       1310       1320
TCTATCGTTA TATCGCAGAA ACACTTAATA CCAAATATTA CGTTTTCTTT AGAGAAAGAA 1330       1340       1350       1360       1370       1380
AATACATCCT TATATTCTTC AAGTTTTATC TTATCAGATA CTACATCTGT ATTAAAAAGT 1390       1400       1410       1420       1430       1440
GCAATTATCT TTATGATATA ATTGCTATCC GCTAGGACTT TATTTATTGT TCTGATAATG 1450       1460       1470       1480       1490       1500
AAACTATTGT TTTCCATTAA TATTTTGTAA GCTTGATGTT CGTTATTAGC ACTTTTAATT 1510       1520       1530       1540       1550       1560
AACGACACAA TTCCTAGTAT CTTTTTTAAA TCCTGCACTA TTTCATTTGT ATCTTTTTTC 1570       1580       1590       1600       1610       1620
ATATTAGAGT ACATATTGTT TATAGATGTA ATAACTTTTG CATATACTAA CATATCTTTA 1630       1640       1650       1660       1670       1680
AATATTCTGA TAAACTGTTC TTTGTTTCT TTATCTGTTA TTTTGTTGAG CATAGATTTT
```

FIG. 3C

```
      1690        1700        1710        1720        1730        1740
ACGTTTGCCG  CTGATCGCAT  ATACCAAAAT  GTAAACATCT  TGAATTCTAC  TTGCTGCATG
             PRIMER 2    ──────────▶
      1750        1760        1770        1780        1790        1800
GCTAGAATAA  CAGTCTCGTC  AGACATTGCG  CAGTTAAATA  CACCGCCTAT  CTTACTTTCT
             PRIMER 1   ──────────▶
      1810        1820        1830        1840        1850        1860
AGAATAGGAA  AAACCGTTAA  AAATGAATCG  ATATCATTAT  CATAATTTAC  TTCATACACT
                                ClaI
      1870        1880        1890        1900        1910        1920
TTTGACCTG   TACTATTCTC  TAAATACTTC  TTACTTAATT  CATAAAATTC  AATAAATGCA
      1930        1940        1950        1960        1970        1980
TTCCTGAACT  TTTCCATGAT  TTATAGCTTG  TAGTATTTT  CTAATATTGA  TTTGATTTGT
            ORF1 ─▼
      1990        2000        2010        2020        2030        2040
ATATGTGTAT  AATCTTTACC  GATACCTAAT  TTAAGCATAG  TATTAATAAC  CCAAGTTTTT
      2050        2060        2070        2080        2090        2100
ATAAATATTT  CTTTGTTATC  GGTTACCACA  TATTTAAATA  CTGAATTAAA  GTATTTAACT
      2110        2120        2130        2140        2150        2160
ATAGGATTAT  TCTGAGTAGA  TATATTATCC  ATAAATACAG  ACCGTTTGT  AGATAGAGGT
      2170        2180
TCTGTAAATA  ATTCACCGTC  GAC
                         SalI
```

Figure 8C:
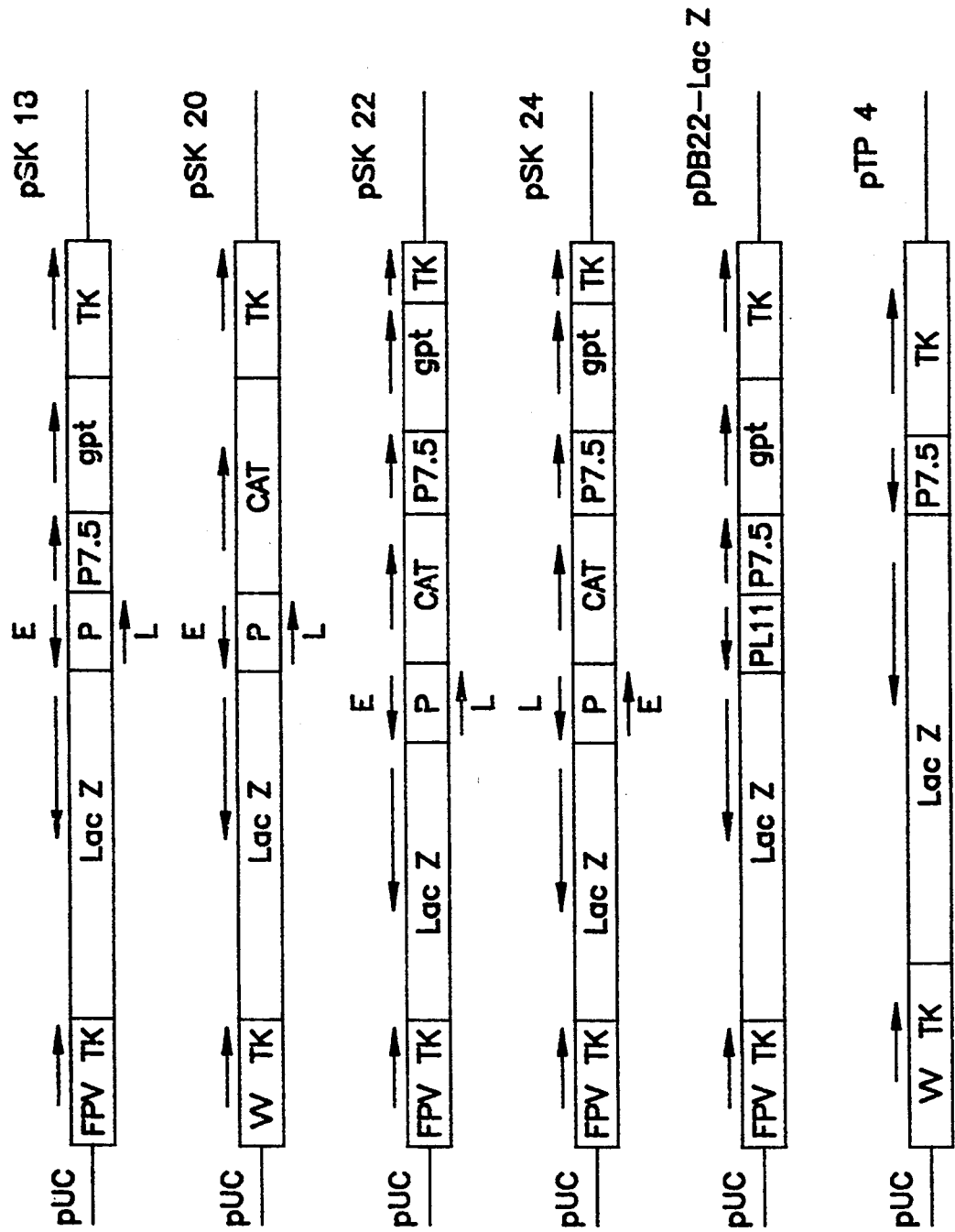

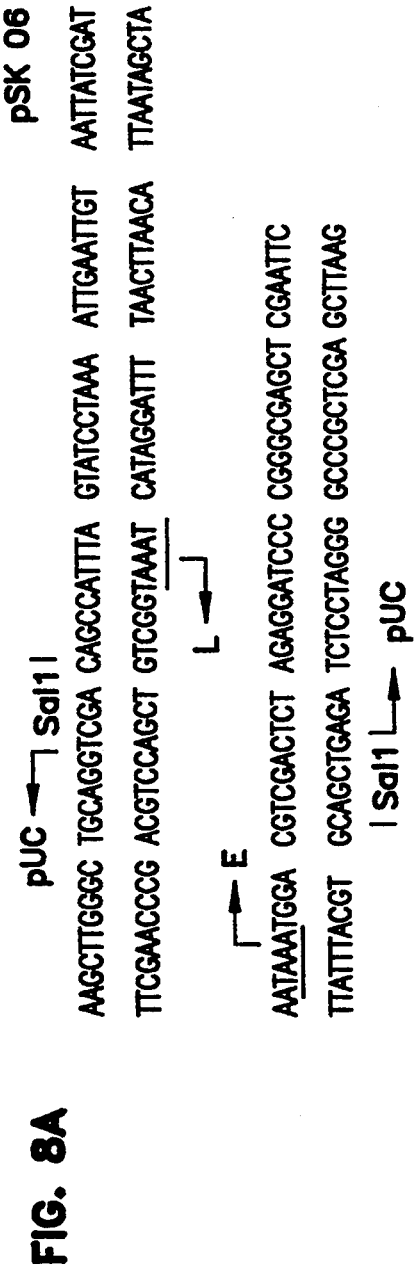
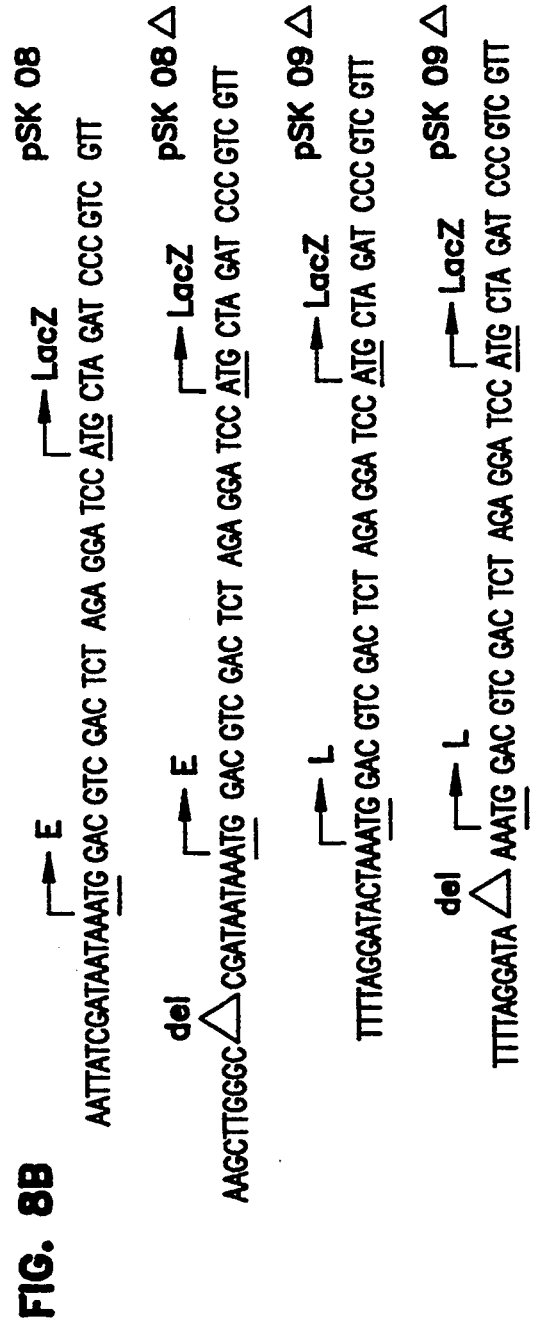
FIG. 8A
FIG. 8B

5'-ATTTAGTATCCTAAAATTGAATTGTAATTATCGATAATAAAT → EARLY
3'-ATTTATTATCGATAATTACAATTAATTTTAGGATACTAAAT → LATE

FIG. 9

POX VIRUS VACCINE

This is a continuation of application Ser. No. 07/582,881, filed Oct. 9, 1990.

This invention relates to recombinant vectors and their construction, and in one aspect this invention relates to recombinant fowlpox virus vectors and use thereof.

Poxviruses are large DNA viruses which replicate within the cytoplasm of infected cells. The vaccinia virus is the most widely studied member of the poxvirus family and has been widely used to express a number of foreign genes inserted into the vaccinia virus genome. In recent years, recognition of non-essential regions of the vaccinia virus genome, followed by mapping and nucleotide sequence determination, has made it possible to insert and express a wide variety of foreign genes through the medium of recombinant vaccinia viruses. Such recombinant vaccinia viruses have the potential to deliver vaccine antigens to a variety of animal species. However, for faithful expression of an inserted gene, it is important to position the gene near unique viral promoter regions.

A recognised problem resides in a risk of cross species infection and therefore the spread of diseases from one animal species to another through the widespread use of vaccinia virus in animals. Thus, the construction of recombinants based on host specific poxviruses is desirable, e.g. fowlpox virus for poultry or ORF for sheep vaccines. Although promoter sequences have been described for a number of early and late genes of vaccinia viruses, little is known about promoter regions in other pox viruses. In order to construct host specific live viral vaccines, it is of fundamental importance that the molecular biology of those viruses, and in particular the biology of transcriptional control elements or promoter region(s) in the pox virus be understood. Therefore, it is necessary to characterise and isolate these regions before utilising them in suitable recombinant vectors. Such vectors show great potential for the manufacture of viral vaccines and the like.

Accordingly, it is an object of the present invention to overcome, or at least alleviate, one or more to the deficiencies and/or difficulties related to the prior art.

Accordingly, in a first aspect of the present invention there is provided a gene sequence including a first promoter for the expression of a major early fowlpox virus protein.

In a preferred aspect of the present invention, the gene sequence further includes a second promoter for the expression of at late fowlpox virus protein in opposite orientation to said first promoter.

The gene sequence may be approximately 40 base pairs in length, consisting of two promoter elements in opposite orientation to each other.

As stated above, this promoter sequence, in its preferred form, is characterised in that it has a major early function and a late function in opposite orientation to the early function. The early function of the promoter compares well with the strongest known promoter of vaccinia virus (PL11). Because of the strength of this promoter and its unique bidirectional nature, it has important applications in the construction of both vaccinia (VV) and FPV vectors and other recombinant poxviruses for the delivery of foreign antigens. Its small and defined size makes it a versatile DNA element which may express two foreign genes of interest simultaneously in a pox virus expression system as described below. Since its early function compares well in strength with PL11, a VV promoter widely used for expression of foreign genes during late stages, of virus growth cycle, it may be a promoter of choice when high levels of expression is required during early stages of virus growth. Its promoter strength is 3–4 times greater than the VV P7.5 promoter which has been widely used, to date, to express genes in recombinant VV, FPV and other poxviruses (for a review see Moss and Flexner, 1987). The gene sequence may be particularly useful to induce cytotoxic T-lymphocyte (CTL) response to an expressed antigen since late promoter expressed gene products appear not be recognised by CTL (Coupar et al., 1986). Being a FPV native promoter, it may be a promoter of choice in developing FPV based vectors for the delivery of vaccine antigens preferably to poultry.

Finally, because of its small and defined size and its unique structure, it may provide an important tool to study the temporal regulation of poxvirus genes.

In a further preferred aspect of the present invention there is provided a gene sequence including a first promoter for the expression of a major early fowlpox virus protein.

Accordingly, in a preferred aspect there is provided a plasmid selected from plasmids pSK06 and pSK07 as hereinbefore described.

Samples of purified DNA containing the plasmid pSK06 were deposited with the Australian Government Analytical Laboratories of 1 Suakin Street, Pymble, New South Wales, 2073, Australia, on 9th February, 1989 and have received the deposition number N89/004621.

The viral vector or derivative thereof may be constructed using a suitable plasmid cloning vector. Suitable plasmid cloning vectors include pUC8, pUC12, M13-mp8 and -mp9.

The native promoter region and fragment of foreign DNA may be flanked by DNA of non-essential regions of the FPV genome. It will be understood that the use of DNA constructs employing native promoter regions of the fowlpox virus not only makes possible the provision of highly host specific viruses, but also provides for a far more efficient virus in terms of its translational efficiency relative to other recombinant pox viruses, all of which to data have employed foreign promoter regions from other sources to initiate expression of selected genes, e.g. promoter regions from a vaccinia virus source.

Accordingly in a preferred aspect, there is provided
a viral vector including a portion of the genome of a vector virus;
a gene sequence including
  a first promoter for the expression of an early fowlpox virus protein; and
  a second promoter for the expression of a late fowlpox virus protein in opposite orientation to said first promoter; and
a first DNA sequence coding for a first foreign gene of interest and under the control of the first promoter.

Preferably the first foreign DNA sequence codes for a first antigen characteristic of an avian disease.

In a preferred embodiment of this aspect of the present invention the viral vector includes alternatively or in addition to said first DNA sequence a second DNA sequence coding for a second foreign gene of interest and under the control of the second promoter.

Preferably the second foreign DNA sequence codes for a second antigen characteristic of an avian disease.

In a particularly preferred form, the portion of the genome of a virus is a portion of the fowlpox virus geneome or vaccinia virus genome.

In a preferred form the plasmid cloning vector may include a DNA sequence of a non-essential region of the FPV genome into which region the suitable native promoter region and fragments of foreign DNA may be inserted.

In this form the native promoter region and promoter of foreign DNA may be flanked by DNA of a non-essentially region of the FPV genome.

Accordingly, the viral vector according to this aspect of the present invention may be utilised in the preparation of vaccines, preferably vaccines against avian disease.

In a further aspect of the present invention there is provided a process for the preparation of a viral vector which process includes
providing
   a viral DNA from a fowlpox virus; and
   a plasmid cloning vector;
constructing a genomic library from the viral DNA;
identifying a gene sequence from the genomic DNA library, said gene sequence including
   a first promoter for the expression of a major early fowlpox virus protein; and
   a second promoter for the expression of a late fowpox virus protein in opposite orientation to said first promoter; and
inserting the gene sequence into a suitable site in the plasmid cloning vector.

In a preferred aspect of the process of the present invention the process may include the step of mapping and sequencing a suitable native promoter region.

In a further preferred aspect of the process of the present invention may further include providing a second suitable plasmid cloning vector.

and subcloning a segment of the first plasmid cloning vector including the native promoter region into the second suitable plasmid cloning vector.

The preferred process may further include further sequencing of the native promoter region.

In a preferred form of the process of the present invention the process may include
providing
   a first suitable plasmid cloning vector,
   a suitable native promoter region,
   a first segment of DNA encoding a non-essential region of FPV genome,
   a second segment of foreign DNA;
cloning the first segment into the suitable plasmid cloning vector,
cloning the native promoter region into the suitable plasmid cloning vector within the first segment of DNA,
cloning the second segment of foreign DNA into the suitable plasmid cloning vector within the first segment of DNA.

It will be understood in this preferred manner the native promoter region and second segment of foreign DNA may be inserted into viable FPV at a previously established region by virtue of the flanking non-essential region of the FPV genome created as described above.

The thus formed sequence may be inserted into FPV virus infected cells utilising any suitable technique for example homologous recombination.

It is to be understood that while the invention hereinbelow describes the isolation and characterisation of early gene of fowlpox virus and the insertion of fowlpox promoter sequences into a plasmid vector, the technology described is equally applicable to the isolation and characterisation and insertion of other native animal pox virus promoter region into suitable recombinant plasmids. These plasmids may then be utilised to produce animal pox virus vaccines.

In the first stage of mapping and sequence of the promoter sequence, in a preferred identification early mRNA's coded by the FPV genome was undertaken. Such identification lead to a major approximately 1.0 kb transcript which was mapped to an approximate 1.5 kb ClaI fragment.

The 1.5 kb fragment was cloned into PUC8 and M13 vectors and sequenced.

Accordingly in a preferred embodiment of the present invention there is provided a fowlpox virus vector including an approximate 1.5 kb ClaI fragment cloned into a suitable plasmid or bacteriophage cloning vector. Such cloning vector may include pUC8, pUC12, M13-mp8 and mp9.

Further identification may be undertaken utilising fragments of the clone which may be sub-cloned into other plasmids and sequenced. The dideoxy chain termination method may be used.

Accordingly, in a steel further embodiment of the present invention comprises a gene sequence including a late RNA start site and an early RNA start site separated by a short sequence of DNA. The gene sequence may constitute a bidirectional promoter cassette.

In a further aspect, the invention may be utilised to provide an avian disease vaccine comprising recombinant fowlpox virus wherein at least a first foreign DNA sequence encoding an antigen characteristic of the said avian disease has been inserted into a suitable gene of the fowlpox virus or in virus DNA sequences controlling expression of said gene, and under the control of at least a first native fowlpox virus promoter region or regions. Referably two foreign DNA sequences maybe included under the control of a bidirectional promoter element on either side in opposite orientation.

It is envisaged that in accordance with the present invention vaccines may become available for protection against a wide variety of avian diseases such as those caused by viruses, bacteria, protozoa, metazoa, fungi and other pathogenic organisms, by insertion of DNA sequences encoding appropriate antigens characteristic of these diseases into the FPV genome as broadly outlined above.

In one aspect, the present invention now makes possible the construction of a biologically safer range of host specific recombinant avian vaccines than hitherto obtainable, which vaccines include native promoter regions of the fowl pox virus.

This invention therefore also offers methods useful in the construction of recombinant fowlpox viruses or related avian poxviruses, which methods are characterized by the introduction of foreign DNA into the fowlpox virus or into virus DNA sequences, which sequences are able to use native FPV promoter regions.

The present invention will now be more fully described with reference to the accompanying examples. It should be understood, however, that the following description is illustrative only and should not be taken in any way as a restriction on the generality of the invention described above.

In the figures

FIG. 1 is a restriction map of PstI fragment F of fowlpox virus genome and mapping of major E-gene within it. The directions of the two ORF's within the 1.5 kb ClaI fragment and one upstream of its are indicated by arrows. ORF1 and 3 represent two late genes while ORF2, the major early gene.

Figure 2:
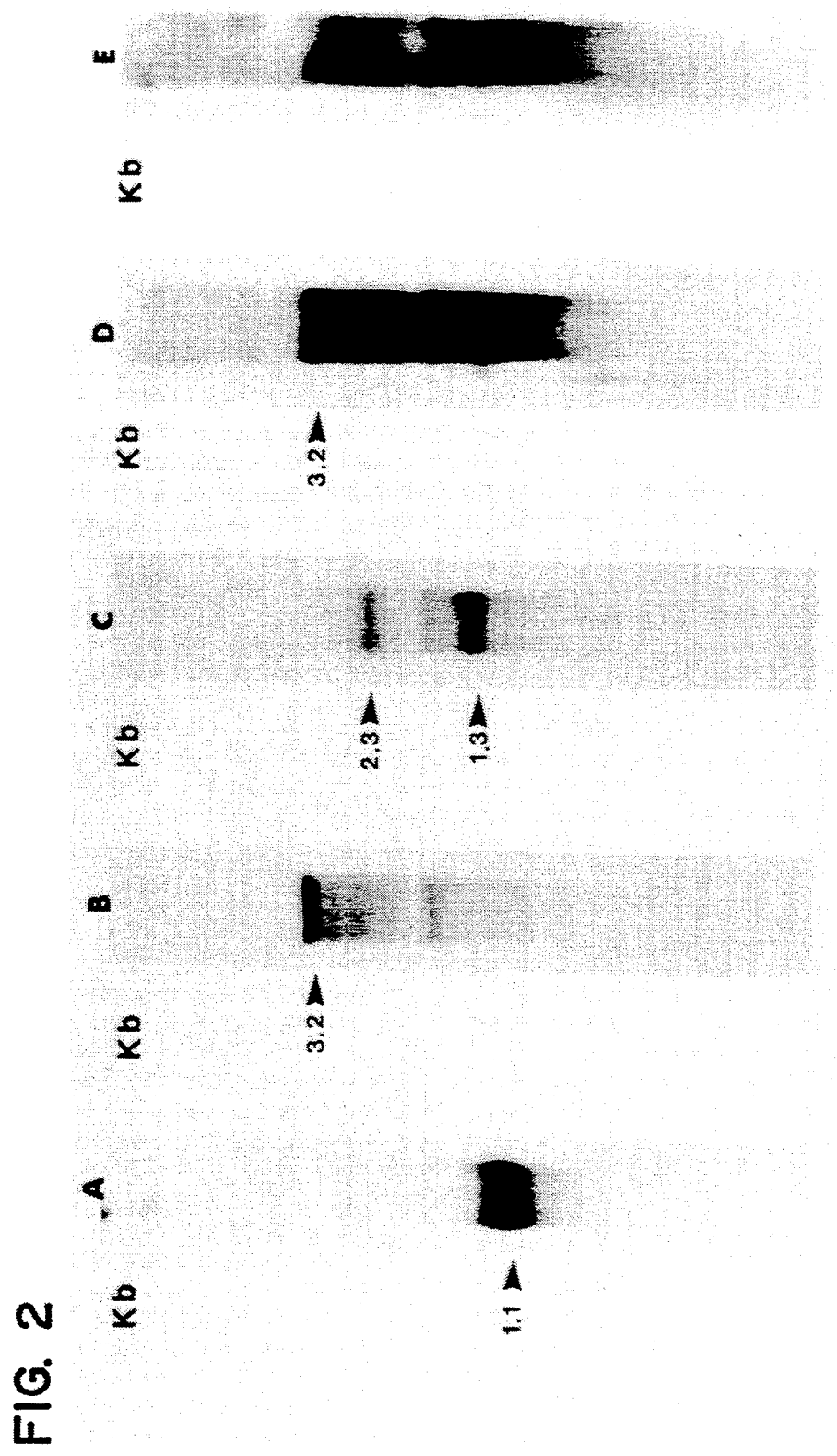

FIG. 2 is a mapping of FPV-PstI fragment F coded early transcripts by northern blot analysis. Total cellular RNA isolated from virus infected cells incubated in presence of AraC was hybridised to gel purified nick translated ClaI fragments of PstI fragment F. A, 1.5 kb; B, 2.0 kb; C, 3.0 kb; D, 4.0 kb and E, 4.8 kb. RNA was electrophoresed on 1.2% agarose, 5.4% formaldehyde denaturing gels and blotted onto Hybond-N nylon membranes prior to hybridization to $^{32}$P-labelled nick translated probes.

FIG. 3, 3A, 3B, 3C is a sequence of 1.5 kb ClaI fragment and the region around its. (SEQ. ID NO: 1) Sequence was obtained from both strands by dideoxy method using Eco R1 and HindIII subclones of 1.5 kb ClaI fragment in M13. The region upstream and downstream of ClaI sites was sequenced using synthetic primers on ss DNA templates from M13 clones containing the 3.7kb SalI fragment (see FIG. 1). The translation start and termination sites for the two ORF's, and location of primers used for S1 nuclease analyses are indicated. The RNA start sites for all three genes are indicated by dotted lines. The two promoter element (E and L) described in the text is boxed in this figure.

Figure 4:
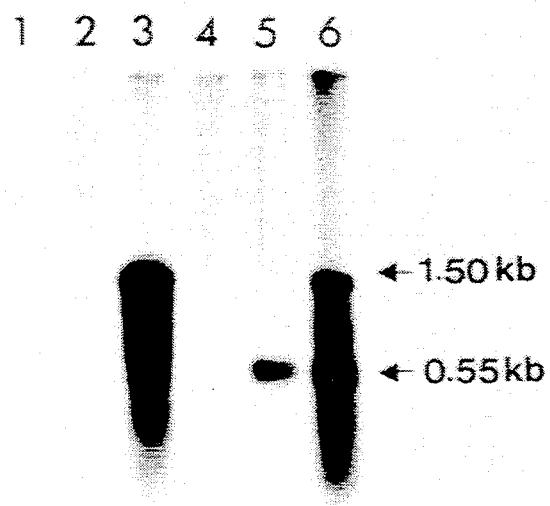

FIG. 4 is a S1 nuclease analysis of 1.5 kb ClaI fragment. Two ss-M13 DNA clones containing the complementary strands of the ClaI fragments (in mp8 and mp9 respectively) were hybridised to total cellular RNA from uninfected host cells (lanes 1 and 4) or FPV infected cells incubated in the presence (lanes 2 and 5) or absence (lanes 3 and 6) of AraC, followed by treatment with S1 nuclease. Protected fragments were fractionated on 1% alkaline agarose gels, transfered to nylon membranes and hybridised to nick translated $^{32}$P-labelled ClaI fragment. M13 mp8 clone (lanes 1–3) is early RNA like strand, while M13 and mp9 clone (lanes 4–6) contains sequence complementary to early gene RNA.

Figure 5A:
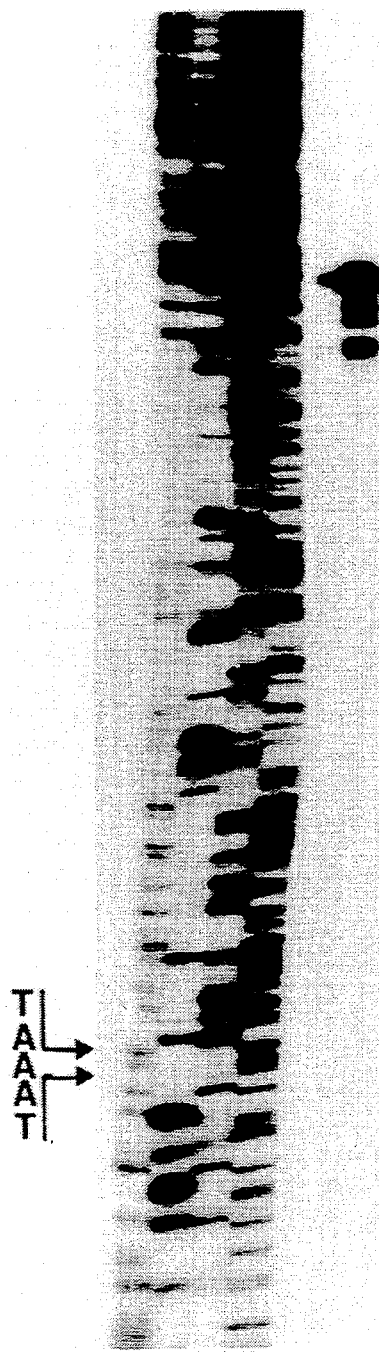
Figure 5B:
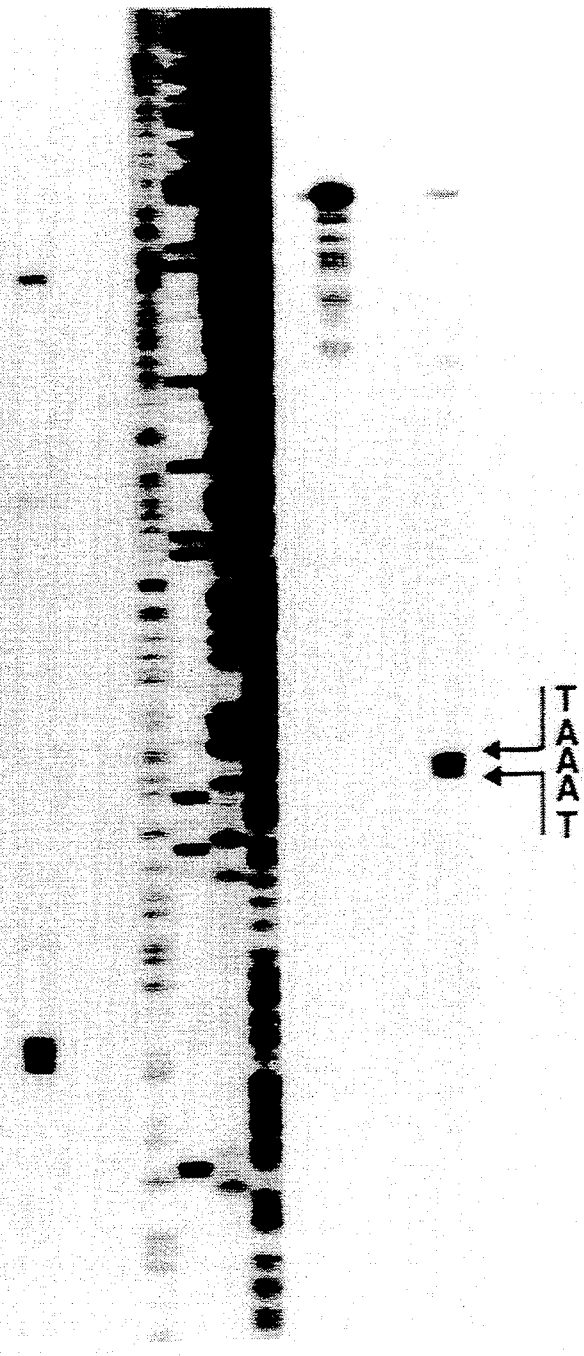

FIG. 5 is a mapping of the 5'-end of the ORF1 coded RNA. Total cellular RNA from uninfected CES cells (Lane 2) of FPV infected cells in the presence (lane 3) or absence (lane 4) of AraC was hybridized to $^{32}$P-labelled ss probe (lane 1). For preparation of probes, synthetic primers complementary to ORF1, 424 (Primer 1) and 482 bp (Primer 2) upstream of the ClaI site were extended in the presence of $^{32}$P-dCTP on ss-M13 DNA clone (M13-Sal 3.7), cut with SalI and relevant DNA fragments isolated from sequencing gels. DNA-RNA hybrids were treated with S1 nuclease and protected fragments ran on 6% sequencing gels alongside a sequencing ladder obtained by same M13 DNA template and primers. Panels A and B represent experiments with primers 1 and 2 respectively. The sequence around the 5'-end of the major protected fragments is shown for the RNA like strand. Technical details of S1 nuclease analysis were according to Davis et al., (1986).

Figure 6:
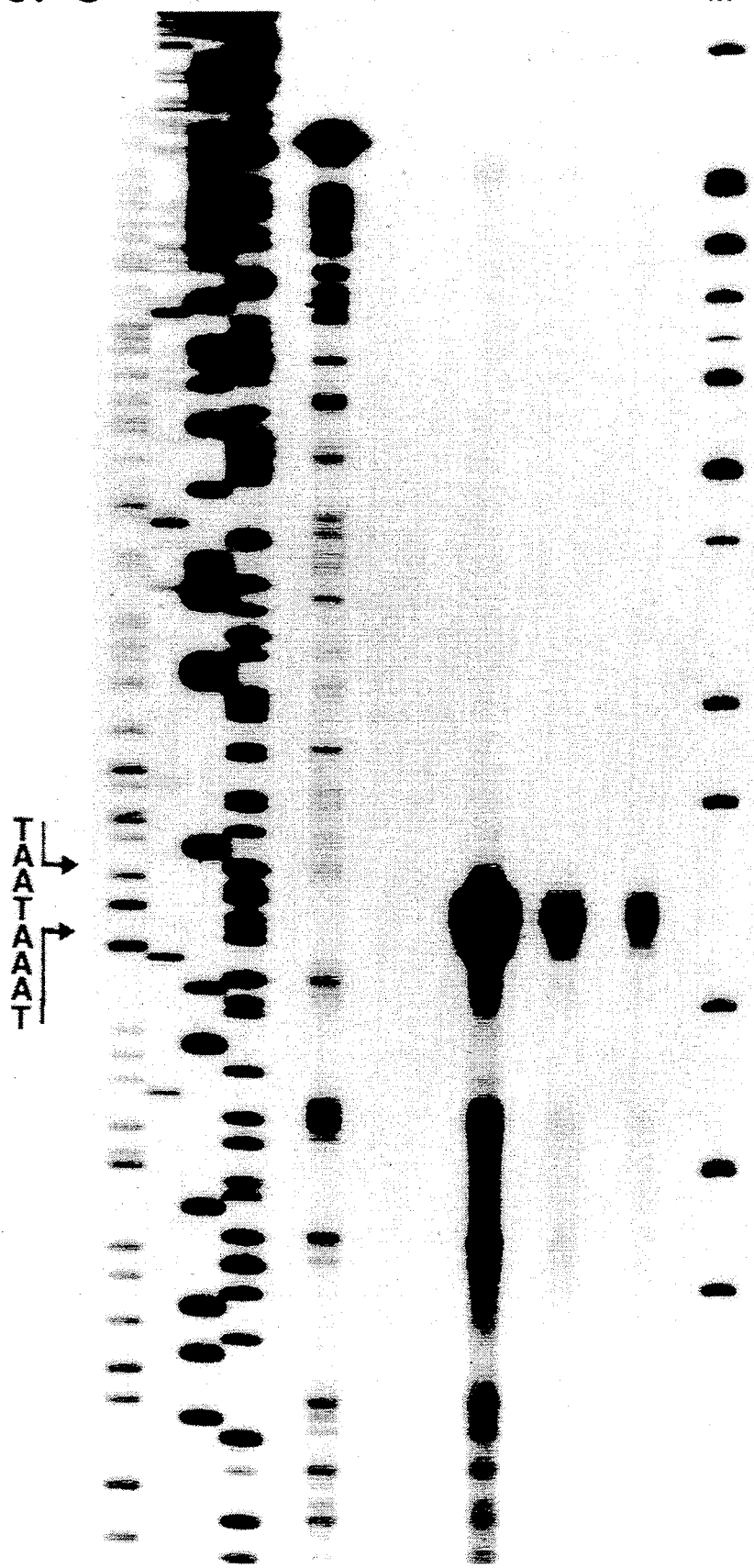

FIG. 6 is a mapping of the 5'-end of ORF2 coded RNA. $^{32}$P-labelled ssDNA probe complementary of RNA like strand were prepared by extending a synthetic primer 124 bp upstream of ClaI site on a M13-Sal 3.7 ssDNA clone followed by digestion with EcoRl and isolation of 453 base probe from sequencing gels. Probe (lane 1) was hybridised to RNA isolated from uninfected cells (lane 2), FPV infected cells incubated in presence of 100 ug/ml cycloheximide (lane 3) or 50 ug/ml AraC (lane 4) or without either (lane 5). Following S1 treatment of DNA-RNA hybrids, the protected fragments were analysed on 6% sequencing gel. DNA markers (M) were prepared by $^{32}$P-labelling of HpaII cut pBR322 fragments. Sequencing ladder on the left hand side was obtained by using the same primer and template as used for preparation of hybridization probe. Sequence around the 5'-end of protected fragments is shown for the RNA like strand.

Figure 7:
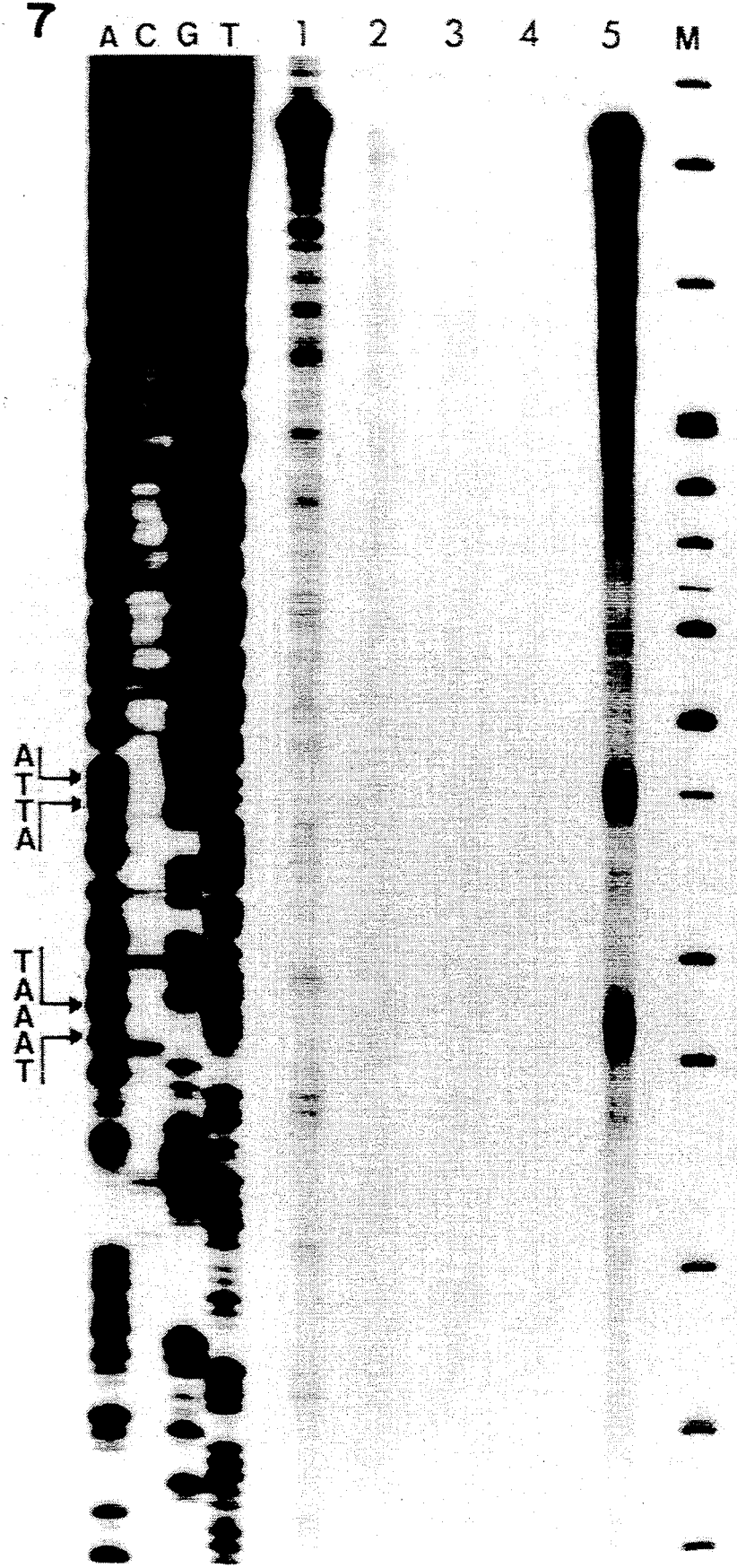

FIG. 7 is a mapping of the 5'-end of ORF3 coded RNA. $^{32}$P-labelled ssDNA probe complementary to the RNA was prepared by extending a synthetic primer 91 bp downstream of ClaI site on a M13-Sal 3.7 ssDNA clone containing the RNA like strand followed by digestion with AccI and isolation of 260 base probe from sequencing gels. Rest of the experimental details were as in FIG. 5. Lane 1, probe alone; lane 2, uninfected cell RNA; lane 3, early RNA (cycloheximide); lane 4, early RNA (AraC); lane 5, late RNA. Markers (M) are same as in FIG. 5. Sequence around two late RNA protected fragments is shown for RNA like strand.

FIG. 8 is a construction of the plasmids used in transient expression experiments. Polylinker regions of pSK06 containing the promoter element (P) in SalI site is shown in panel A (SEQ. ID. NO: 2; SEQ. ID NO: 2) The direction of early and late transcription are indicated and early and late RNA start sites are underlined. In pSK07, from which pSK09 and pSK22 were derived, the orientation of SalI fragment is relation to polylinker, was opposite to that in pSK06; pSK08 (SEQ ID NO:4) and pSK09 (SEQ ID. NO: 6) were constructed by cloning E. coli LacZ gene into the Bam HI site of pSK06 and pSK07 respectively (B). The sequence around promoter-LacZ junction for pSK08 (SEQ. ID. NO:5) and pSK09 (SEQ ID. NO: 7) deletion mutants used in transient expression system is also shown. The basic structure of other plasmids used in experiments detailed in Tablet 3 is shown in panel C. In the figures in panel C, promoter and gene fragments are not proportionate to their actual sizes.

FIG. 9 is an alignment of early and the late promoter elements of FPV.

EXAMPLE 1

Identification and Mapping of the Major Early Gene

FPV encoded early mRNA's were detected by hybridizing total cellular RNA prepared from FPV infected CES cells grown in the presence of AraC to four cloned PstI fragments of the FPV genome. Four fragments E, F, J and M (20.5, 17.3, 12.5 and 5.7 kb respectively) representing approximately 1/6th of the total genome of FPV (Coupar et al., unpublished) were analysed and eleven early transcripts were identified by norther blot analysis of RNA (Table 1), of which four hybridised to fragment F. The restriction enzyme map of fragment F is shown in FIG. 1. To map the early transcripts within the 17.3 kb fragment F, 5 size fractionated ClaI fragments of 4.8, 4.0, 3.0, 2×2.0 and 1.5 kb respectively were hybridized to early RNA (FIG. 2). The major RNA transcript (approximately 1.0 kb) was mapped to the 1.5 kb fragment. Three other early transcripts of 3.2, 2.3 and 1.2 kb respectively were also detected. The quantity of this transcript is approximately 10 fold higher than any of the other transcripts hybridizing to the four PstI fragments of the FPV genome used in the study.

Sequencing of ClaI fragment

The 1.5 kb ClaI fragment was cloned into the AccI site of pUC 8, released as an EcoRI/Hind III fragment and recloned into M13 mp8 and mp9. The EcoRI and HindIII fragments of the clone were also subcloned into M13 vectors and the complete sequence of 1.5 kb ClaI fragment obtained by sequencing both strands is shown in FIG. 3 (SEQ ID NO: 1). The sequence consisted of two open reading frames (ORF's), one (ORF1) extending beyond the ClaI site (1101 bp) and the other (ORF2) in the opposite orientation (501 bp) contained solely within 1.5 kg ClaI fragment. To ascertain which one of these ORF's codes for the early RNA, two single stranded M13 clones consisting of complementary strands of the 1.5 kb ClaI fragments were hybridized to early and late RNA from FPV infected cells, treated with S1 nuclease, electrophoresed on alkaline denaturing gels, transferred to nylon membranes and hybridised to nick-translated ClaI fragment. The mp8 clone (complementary to ORF1) protected a 1.5 kb late RNA while the mp9 clone (complementary to ORF2) protected one 0.55 kb early RNA and two 1.50 kb and 0.55 kb fragments with late RNA's. This indicated that ORF1 and ORF2 code for a late and an early/late transcript respectively. The 0.55 kb protected fragment late in the infection (FIG. 4, lane 6) possibly represents the presence of stable early message. The longer protected fragment of 1.5 kb in lens 6 could either be a transcript originating from the same start point as early transcript and terminating downstream of distal ClaI site, or a late transcript originating upstream of proximal ClaI site (upstream of the early gene initiation point). Since pox virus late genes lack defined termination signals, giving rise to transcripts with heterogenous 3' ends (Moss, 1985), the 1.5 kb protected fragment in lane 6 of FIG. 4 could have only originated from a late RNA start site near or upstream of the early start site. From S1 nuclear analysis (see below) it was apparent that the former possibility is true.

Analysis of the 5'-end of the ORF1 Coded RNA

It was apparent from data represented earlier (FIG. 4) that ORF1 codes for a plate RNA. In order to determine the 5'-end of this late gene, two synthetic oligomers complementary to late RNA like strand (Primers 1 and 2, FIG. 3) were extended on M13 clone consisting of the 3.7 kb SalI fragment (FIG. 1) in the presence of $^{32}$P-dCTP. ssDNA probes complementary to late transcript were hybridised to early and late RNA from FPV infected cells followed by S1 nuclease treatment (FIG. 5). It is clear from FIG. 5 that only late RNA protected the probe and the major protected product mapped to a 'TAAAT' sequence near the translation start site (FIG. 3) (SEQ ID NO:1).

Analysis of the 5'-end of the ORF2 Coded RNA's

For the 5'-end analysis of the gene, a probe was prepared using a primer (primer 3, FIG. 3) upstream of the ClaI site and extending it on a ss-M13-Sal3.7 DNA clone which excompasses the complete ClaI fragment (FIG. 1). The 5'-end of the protected fragment by immediately early, early and late RNA mapped to a sequence TAAAT near the ATG of ORF2 (FIG. 6). Since there were no late RNA protected fragments of larger size, it appears that both early and late RNA shown in FIG. 4, initiate at the same start point. This is, to our knowledge, the first poxvirus promoter described where the same initiation site is recognised by RNA polymerase both during early and late stages of infection. However, the immediately early function of the gene appears to be the major aspect of the gene and for this reason and to avoid confusion, this promoter with early/late function has been referred as early promoter in the following text.

Presence of a Late Promoter Function Upstream and in Opposite Orientation to ORF2

The sequencing of DNA upstream of the ClaI site revealed the presence of an ORF starting 35 bp from the early start site and in opposite orientation (ORF3, FIG. 3). The start of ORF3 consists of a 'TAAAT' motif, suggesting that it would transcribe a late mRNA. The S1 nuclease analysis of the 5'-end of this late gene revealed that only late RNA protected the probe from S1 digestion (FIG. 7). Major products mapped to the predicted 'TAAAT' motif upstream of the ATG while another major product mapped to a sequence 30 bp upstream (ATTA). There were several larger protected fragments all the way up to the size of probe and these possibly represent the heterogeneous 3'-ends of late transcript originating from ORF1. Since the late transcript maps to the sequence 30-35 bp upstream of the early start site, the sequence between the two start sites constituted a potential bidirectional promoter element, having both early/late and late function in opposite orientations.

40 bp and DNA are Sufficient for Expression of Both Early and Late Genes

In order to assess the promoter activities, DNA sequence comprising of both early and late start sites and the first two amino acid codons (ATG and the following 3 bases) flanked by SalI linkers were synthesized and cloned into the SalI site of pUC12 in both orientations (FIG. 8). The first two codons of ROF's were included since the start site of both head to head genes map very close to the translation start site. A BamHI fragment from pGH101 consisting of a LacZ gene of E. coli (Herman et al., 1986) was then placed downstream of the promoter element (into the BamHI site) of pUC 12 linker. These vectors were designed in such a way that the ATG of LacZ was in frame with the ATG of the respective promoters (FIG. 8). These plasmids were then used in a VV transient expression system to assess the promoter strengths by the levels of B gal expressed (Table 2). The results indicated that high levels of B gal were expressed by the both early and late promoter elements. The temporal regulation of the promoter was also maintained and thus the early promoter activity was not affected by inclusion of AraC, and inhibition of DNA synthesis, while the late promoter activity was completely abolished (Table 2). Results also show that in CV-1 cells, the activity of early promoter is approximately 5-6 fold higher than that of late promoter. In a mutant of the early promoter where the region between ClaI and PstI site of pSK08 was deleted the activity of the early promoter was almost completely abolished (Table 2). Also deletion of 2 bp rear the start site of late promoter abolished the activity of the late promoter (Table 2).

Assessment of the Activity of FPV—Early Promoter Relative to Vaccinia Virus Promoters Two widely used and well characterized promoters of VV, PL11 (late) and P7.5 (early/late) were used in a transient expression system to compare their activity with the FPV-early promoter. Constructs consisting of LacZ under control of PL11 (pDB22-LacZ) and P7.5 (pTP4) have been described and contain the LacZ-promoter chimera, flanked by either the FPV (pDB22-LacZ) or VV (pTP4) TK gene. pDB22-LacZ also contains an E. coli gpt gene under control of P7.5. Analogous plasmid constructs were made using the early promoter and LacZ gene, and used in the transient B-gel expression system. The results are shown in Table 3. It is clear from the data that the transfection of all plasmids result in significant amounts of B-gal activity in the transient expression system.

In pSK18, 20 and 22 where LacZ was placed under control of early-promoter element of FPV, flanked by either VV of FPV TK gene product comparable B-gal activities. In the presence of AraC, an apparent accumulation of B-gal occurs, as was evident also from data in Table 2. Again the activity of late promoter element of FPV was about 1/5th of the early-promoter activity. When compared with two of the most used promoters of VV, P7.5 and PL11, the early-promoter activity was about 3.5 fold higher than that of P7.5 and approximately same to PL11. Since PL11 is the strongest known promoter of VV, the early FPV promoter is thus equally efficient. It is also clear from the data in Table 2 that the temporal regulation of all the promoters is maintained under transient expression conditions since in all cases, inhibition of DNA synthesis of AraC caused the block in late promoter activity. However, P7.5 an early/late promoter of VV only appeared to work late in the infection in our transient a expression system, as has been observed by others (Chakrabarti et al., 1985).

Structure of the FPV Promoter Element it is clear from the data presented earlier that only 34 bp of DNA sequence between the early and late gene start sites (between 2-ATG's) is sufficient for the transcription of the early and late genes respectively. Since early and late promoters of pox viruses appear to be quite different (Smith et al. 1984) the FPV promoter element could be used in determining the DNA domains required for temporal regulation of pox virus early and late genes. It is evident from the results presented that a mutation near the early start site or within the TAAAT motif of late start site almost completely abolish their respective transcription function (Table 2). Fox virus late promoters are characterised by a highly conserved 'TAAAT' motif which is an essential cia acting element (Hanggi et al., 1986; Rosel et al., 1986). Thus the late promoter of FPV is similar to other reported pox virus late promoter elements. The interesting aspect of the FPV promoter element however is that early start site also maps to a TAAAT mofif. The 5'- 3' alignment of the two strands of FPV promoter element show remarkable degree of similarity (FIG. 9) (SEQ. ID NO:8, SEQ ID NO:9). Out of 42 bases aligned, 28 bases match up perfectly without any deletion or substitution. The A-T content of the promoter element is 83% which is comparable to the sequences of other pox-virus promoters (Weir and Moss, 1983; Mars and Beaud, 1987; Lee-Chan et al., 1988). Besides this similarity, there are no remarkable DNA elements within the promoter region, upstream of RNA start site.

LITERATURE CITED

1. Moss, B. and Flexner, C., (1987) Annu. Rev. Immunol. 5, 305–324.
2. Coupar, B. E. H. et al. (1986) Eur. J. Immunol. 16, 1479–1487.
3. Moss, B. (1985) In: Virology (Fields, B. N. ed.) pp. 685–703. Raven Press. N.Y. and London.
4. Davis. L. G. et al. (1986) Basic method in molecular biology, Elsevier Science Publishing, N.Y.
5. Herman, G. E. et al. (1986) Nucleic Acids Res. 14, 7130.
6. Chakrabarti, S. et al. (1985) Mol. Cell. Biol. 5, 3404–3409.
7. Miller, J. H. (1872) Experiments in molecular genetics, Cold Spring Harbour Laboratory, Cold Spring Harbour, N.Y.
8. Smith, G. L. et al., (1984) Biotech. Genet. Engg. Rev. 2, 383–407.
9. Hänggi, M. et al., (1986) EMBO J. 5, 7071–1076.
10. Rosel, J. L. et al., (1986) J. Virol. 60, 436–449.
11. Weir, J. P. and Moss, B. (1983) J. Virol. 46, 530–537.
12. Mars., M. and Beaud, G. (1987) J. Mol. Biol. 198, 619–631.
13. Lee-Chen, G. J. et. al., (1988) Virology 163, 64–79.

TABLE 1

Approx. sizes of early transcripts hybridizing to four PstI fragments of FPV genome. Total cellular RNA isolated from FPV infected cells in presence of AraC was hybridized on northern blots to nick tanslated clones PstI fragments of the FPV genome.

| PROBE | PstI fragment and its size (kb) | Approx. sizes of early transcripts (kb) |
|---|---|---|
| pTT55 | E (20.5) | 2.0, 1.7, 1.2 and 0.8 |
| pTT63 | F (17.3) | 3.2, 2.3, 1.3 and 1.0 |
| pTT28 | J (12.5) | 3.5, 2.4 and 1.7 |
| pTT68 | M (5.7) | Not detected |

TABLE 2

Activity of B-galactosidase in plasmid constructs in VV-transient expression system. E and L are Early and late promoter elements respectively and Δ represent mutations (see below). Transient expression experiments were carried out according to Chakrabarti et al (1985) using CV-1 cells and 25 ug of plasmid DNA. B-gal activity assayed by the method of Miller (1972) is expressed as umol of ONP produced/3 × $10^6$ cells/30 min at 28° C. The values represent mean of three estimations from the same experiment. pSK08 was generated by deleting the ClaI/PstI fragment of PSK08. In pSK09 two bases, (CT) near the RNA start site (TA<u>CT</u>AAATG) have been deleted creating TAAAATG sequence (Fig. 8)

| | B-gal activity | |
|---|---|---|
| Plasmid Construct | −AraC (Late) | +AraC (Early) |
| pSK 08 (LacZ-E) | 35.78 | 50.78 |
| pSK 08 (LacZ-EΔ) | 0.13 | 0.00 |
| pSK 09 (LacZ-L) | 6.50 | 0.27 |
| pSK 09 (LacZ-LΔ) | 0.27 | 0.00 |
| pSK 08 (no virus infection) | 0.00 | 0.01 |

TABLE 3

Activity of B-galactosidase in plasmid constructs containing VV or FPV promoters in VV transient expression system. E and L are early and late elements of FPV promoter. Plasmids pSK20, 22 and 24 also contain a CAT gene opposite to LacZ. For details see text and Fig. 8 Experimental details are as in Table 2. B-gal activity is expressed as umol of ONP produced/ $3 \times 10^6$ cells/30 min at 28° C.

| Plasmid Construct | | B-gal activity | |
|---|---|---|---|
| | | −AraC (Late) | +AraC (Early) |
| pSK 18 | (LacZ-E, FPV-TK) | 25.10 | 34.44 |
| pSK 20 | (LacZ-E, VV-TK) | 26.70 | 32.50 |
| pSK 22 | (LacZ-E, FPV-TK) | 24.50 | 29.40 |
| pSK 24 | (LacZ-L, FPV-TK) | 4.6 | 0.27 |
| pTP4 | (LacZ-P7.5, VV-TK) | 7.2 | 0.4 |
| pDB22-LacZ | (LacZ-PL11, FPV-TK) | 24.8 | 0.27 |
| pSK 22 | (no virus) | 0.03 | 0.01 |

Finally, it is to be understood that various other modifications and/or alterations may be made without departing from the spirit of the present invention as outlined herein.

We claim:

1. A vaccine including a viral vector, said viral vector including:
   a portion of the genome of a vector virus;
   a bidirectional promoter element including a first promoter which controls expression of an early viral protein in fowlpox virus and a second promoter which controls expression of a late viral protein in fowlpox virus, said second promoter being in an opposite orientation to said first promoter, wherein said bidirectional promoter element has the sequence

5'AGCCATTTAGTATCCTAAAATTGAATT-
   GTAATTATCGATAATAAATGCAC 3' (SEQ
   ID NO: 10)

3'TCGGTAAATCATAGGATTTTAACT-
   TAACATTAATAGCTATTATTTACCTG 5'
   (SEQ ID NO: 11)

and a first foreign DNA sequence coding for a first foreign gene of interest and under the control of said first promoter; or
   a second foreign DNA sequence coding for a second foreign gene of interest and under the control of said second promoter; or
   a first foreign DNA sequence coding for a first foreign gene of interest and under the control of said first promoter together with a second foreign DNA sequence coding for a second foreign gene of interest and under the control of said second promoter.

2. A vaccine including a viral vector according to claim 1, wherein the portion of the genome of a virus is a portion of the fowlpox virus genome or vaccinia virus genome.

3. A vaccine including a viral vector according to claim 1, wherein the first foreign DNA sequence codes for a first antigen characteristic of an avian disease.

4. A vaccine including a viral vector according to claim 1, wherein the second foreign DNA sequence codes for a second antigen characteristic of an avian disease.

* * * * *

UNITED STATES PATENT AND TRADEMARK OFFICE
CERTIFICATE OF CORRECTION

PATENT NO. : 5,368,855

DATED : November 29, 1994

INVENTOR(S) : Boyle et al.

It is certified that error appears in the above-identified patent and that said Letters Patent is hereby corrected as shown below:

On the title page, item [30], insert -- Feb. 10, 1989 [WO] WIPO ..... ..............PCT/AU89/00055 --

In column 1, line 5, insert --, now Pat. No. 5,258,294-- after "1990".

In column 3, line 7, "geneome" should be --genome--; in lines 14 and 15, "non-essentially" should be --non-essential--.

In column 4, line 10, "region" should be --regions--; line 31, "steel" should be --still--.

In column 5, line 22, "its" should be --it--.

In column 6, line 31, "NO:2) should be --NO:3).--.

In column 7, line 43, "nuclear" should be --nuclease--; line 49, "for a plate" should be -- for a late --.

In column 8, line 43, "ROF's" should be --ORF's--; line 66, "rear" should be --near--.

In column 9, line 15, "B-gel" should be --B-gal--; line 42, "it" should be --It--; line 54, "Fox" should be --Pox--; line 55, "cia" should be --cis--.

UNITED STATES PATENT AND TRADEMARK OFFICE
CERTIFICATE OF CORRECTION

PATENT NO. : 5,368,855

DATED : November 29, 1994

INVENTOR(S) : Boyle et al.

It is certified that error appears in the above-identified patent and that said Letters Patent is hereby corrected as shown below:

In column 10, line 18, "3404" should be --3403--; line 63 (3rd col.), "50.78" should be --50.75--.

In column 15, line 13 (Sequence 5), "psk08" should be --psk08Δ--; line 50 (Sequence 7), "psk09" should be --psk09Δ--.

In column 19, line 22, "AAATGCAC" should be --AAATGGAC--.

In column 19, line 24, "TCGGTAAAT" should be -- TCGGTAAAT --

Signed and Sealed this

Fourth Day of March, 1997

BRUCE LEHMAN

*Attest:*

*Attesting Officer*   Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 2183 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: 1.5 Kb ClaI fragment from fowl pox virus genome ( x i ) SEQUENCE DESCRIPTION: SEQ ID NO:1:

```
GGTCCTAAAT TTTGGTGGAT AAGGCAAATT ACTGCTTTGT TGATTGTTAA ATCTATTAAG      60
AAAACTGGTA AAAATACCAG CAGTATCGTT ACTACGTAAT ATAGATATCA TTCTATCCTG     120
AATAGACCTA CTATCGTCTG TATTGTATTC GTCTACTATA GATTCCTTCT CATTTGTACT     180
ATCATCTTCA TCTAGCTTTT CTGAAAATAT CTCTGGATTA TTACTAACAT TACGTTTGAT     240
TCTAGAAATA AAATCTTTGT GGAAGTTCTC AGCCATTTAG TATCCTAAAA TTGAATTGTA     300
ATTATCGATA ATAAATGGAC AATTCTATGG ATATTAACGA TATACTACTG TCAGATGATA     360
ACGATTATAA GAGTTACGAT GAAGATGATG ACTCTATATC CGATATAGGA GAAACAAGTG     420
ATGATTGTTG TACGACTAAA CAATCGGATT CCAGGATAGA ATCTTTCAAG TTCGATGAAA     480
CTACTCAATC ACCTCATCCA AAACAATTGA GCGAAAGGAT AAAGGCTATA AACAACGAT      540
ACACTAGACG TATAAGCCTA TTTGAAATAA CTGGAATTTT ATCCGAAAGT TATAATTTAT     600
TACAACGTGG AAGAATTCCA TTACTTAATG ACCTGACAGA AGAAACGTTT AAAGATTCAA     660
TTATTAATAT TATGTTTAAA GAAATAGAAC AAGGAAATTG TCCTATAGTT ATACAAAAGA     720
ATGGAGAACT TTTATCCTTA ACCGACTTTG ATAAAAAAGG AGTACAGTAT CATCTGGACT     780
ACATTAAAAC TATATGGCGT AACCAACGTA AATTATAATT TAGATATATA ATGTTCTTGA     840
ATAAAATCGA ATATGAATTC TATATCTACA GCATTTCTT TATAGTTAAT GTTGTAATTA     900
TCGGTTATAC ATTGAACAAT TGATATAAGT GTTGTTTTGT GCTTTTCATA TTCTTCCACA     960
AATATGTTTT TATACATTTC ACGGTTATTT GATATCTCAC TTATCAATCC CTGAATGTTA    1020
TTAACCTTTC TTTTCTTTAA ATCTTCTACG GAAACTTTAG TCTTAAATGA TGCCATTATT    1080
TCACTAAAAA GAACGTGTAA GCGTTCGTTA GTAAGTATTT CAGAATACAC TATACTAGAG    1140
AGTTTAGAAA ATATGTTAAC AAATTGTGTT GTTTTGACAC AGCTAGTTTG AAATAAAATA    1200
ATATTAGGTA ATACCTTTTT AAAGAAGCTT ACGTATTTAT TATTTATCTG GTCTATACCG    1260
TCTATCGTTA TATCGCAGAA ACACTTAATA CCAAATATTA CGTTTTCTTT AGAGAAAGAA    1320
```

```
AATACATCTT TATATTCTTC AAGTTTTATC TTATCAGATA CTACATCTGT ATTAAAAAGT    1380

GCAATTATCT TTATGATATA ATTGCTATCC GCTAGGACTT TATTTATTGT TCTGATAATG    1440

AAACTATTGT TTTCCATTAA TATTTGTAA  GCTTGATGTT CGTTATTAGC ACTTTTAATT    1500

AACGACACAA TTCCTAGTAT CTTTTTAAA  TCCTGCACTA TTTCATTTGT ATCTTTTTTC    1560

ATATTAGAGT ACATATTGTT TATAGATGTA ATAACTTTG  CATATACTAA CATATCTTTA    1620

AATATTCTGA TAAACTGTTC TTTTGTTTCT TTATCTGTTA TTTTGTTGAG CATAGATTTT    1680

ACGTTTGCCG CTGATCGCAT ATACCAAAAT GTAAACATCT TGAATTCTAC TTGCTGCATG    1740

GCTAGAATAA CAGTCTCGTC AGACATTGCG CAGTTAATAT CACCGCCTAT CTTACTTTCT    1800

AGAATAGGAA AAACCGTTAA AAATGAATCG ATATCATTAT CATAATTTAC TTCATACACT    1860

TTTTGACCTG TACTATTCTC TAAATACTTC TTACTTAATT CATAAAATTC AATAAATGCA    1920

TTCCTGAACT TTTCCATGAT TTATAGCTTG TAGTATTTTT CTAATATTGA TTTGATTTGT    1980

ATATGTGTAT AATCTTTACC GATACCTAAT TTAAGCATAG TATTAATAAC CCAAGTTTTT    2040

ATAAATATTT CTTTGTTATC GGTTACCACA TATTTAAATA CTGAATTAAA GTATTTAACT    2100

ATAGGATTAT TCTGAGTAGA TATATTATCC ATAAATACAG ACCGTTTTGT AGATAGAGGT    2160

TCTGTAAATA ATTCACCGTC GAC                                           2183
```

( 2 ) INFORMATION FOR SEQ ID NO:2:

( i ) SEQUENCE CHARACTERISTICS:
        ( A ) LENGTH: 107 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
AAGCTTGGGC TGCAGGTCGA CAGCCATTTA GTATCCTAAA ATTGAATTGT AATTATCGAT    60

AATAAATGGA CGTCGACTCT AGAGGATCCC CGGGCGAGCT CGAATTC                  107
```

( 2 ) INFORMATION FOR SEQ ID NO:3:

( i ) SEQUENCE CHARACTERISTICS:
        ( A ) LENGTH: 107 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
GAATTCGAGC TCGCCCGGGG ATCCTCTAGA GTCGACGTGC ATTTATTATC GATAATTACA    60

ATTCAATTTT AGGATACTAA ATGGCTGTCG ACCTGCAGCC AAGCTT                   107
```

( 2 ) INFORMATION FOR SEQ ID NO:4:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: psk08

( i x ) FEATURE:
        ( A ) NAME/KEY: CDS
        ( B ) LOCATION: 40..57

( x i ) SEQUENCE DESCRIPTION: SEQ ID NO:4:

AATTATCGAT AATAAATGGA CGTCGACTCT AGAGGATCC ATG CTA GAT CCC GTC    54
                               Met Leu Asp Pro Val
                               1         5

GTT    57
Val ( 2 ) INFORMATION FOR SEQ ID NO:5:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( i i ) MOLECULE TYPE: DNA (genomic)

( v i i ) IMMEDIATE SOURCE:
    ( B ) CLONE: psk08

( i x ) FEATURE:
    ( A ) NAME/KEY: CDS
    ( B ) LOCATION: 44..61

( x i ) SEQUENCE DESCRIPTION: SEQ ID NO:5:

AAGCTTGGGC CGATAATAAA TGGACGTCGA CTCTAGAGGA TCC ATG CTA GAT CCC    55
                                  Met Leu Asp Pro
                                  1

GTC GTT    61
Val Val
5

( 2 ) INFORMATION FOR SEQ ID NO:6:

( i ) SEQUENCE CHARACTERISTICS:
    ( A ) LENGTH: 56 base pairs
    ( B ) TYPE: nucleic acid
    ( C ) STRANDEDNESS: single
    ( D ) TOPOLOGY: linear ( i i ) MOLECULE TYPE: DNA (genomic)

( v i i ) IMMEDIATE SOURCE:
    ( B ) CLONE: psk09

( i x ) FEATURE:
    ( A ) NAME/KEY: CDS
    ( B ) LOCATION: 39..56

( x i ) SEQUENCE DESCRIPTION: SEQ ID NO:6:

TTTTAGGATA CTAAATGGAC GTCGACTCTA GAGGATCC ATG CTA GAT CCC GTC    53
                              Met Leu Asp Pro Val
                              1        5

GTT    56
Val ( 2 ) INFORMATION FOR SEQ ID NO:7:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( i i ) MOLECULE TYPE: DNA (genomic)

( v i i ) IMMEDIATE SOURCE:
    ( B ) CLONE: psk09

( i x ) FEATURE:

(A) NAME/KEY: CDS
(B) LOCATION: 37..54

(xi) SEQUENCE DESCRIPTION: SEQ ID NO:7:

TTTTAGGATA AAATGGACGT CGACTCTAGA GGATCC ATG CTA GAT CCC GTC GTT    54
                                        Met Leu Asp Pro Val Val
                                        1               5

(2) INFORMATION FOR SEQ ID NO:8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Early fowl pox virus promoter (xi) SEQUENCE DESCRIPTION: SEQ ID NO:8:

ATTTAGTATC CTAAAATTGA ATTCTAATTA TCCATAATAA AT    42

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Late fowl pox virus promoter (xi) SEQUENCE DESCRIPTION: SEQ ID NO:9:

ATTTATTATC GATAATTACA ATTCAATTTT AGGATACTAA AT    42

(2) INFORMATION FOR SEQ ID NO:10:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: Early fowl pox promoter (xi) SEQUENCE DESCRIPTION: SEQ ID NO:10:

AGCCATTTAG TATCCTAAAA TTGAATTGTA ATTATCGATA ATAAATGGAC    50

(2) INFORMATION FOR SEQ ID NO:11:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: DNA (genomic)

(vii) IMMEDIATE SOURCE:
        (B) CLONE: Late fowl pox promoter (xi) SEQUENCE DESCRIPTION: SEQ ID NO:11:

GTCCATTTAT TATCGATAAT TACAATTCAA TTTTAGGATA CTAAATGGCT    50